United States Patent [19]

Colligan et al.

[11] Patent Number: 5,669,490
[45] Date of Patent: Sep. 23, 1997

[54] SUTURE RETAINER

[75] Inventors: Francis D. Colligan, New Haven; Ronald H. Belcourt, Jr., Meriden, both of Conn.

[73] Assignee: United States Surgical Corporation, Norwalk, Conn.

[21] Appl. No.: 474,694

[22] Filed: Jun. 7, 1995

[51] Int. Cl.⁶ ................................................. B65D 85/00
[52] U.S. Cl. .................... 206/63.3; 206/227; 206/380; 206/388
[58] Field of Search ............................ 206/63.3, 227, 206/363, 380, 382, 388

[56] References Cited

U.S. PATENT DOCUMENTS

| | | |
|---|---|---|
| 3,062,372 | 11/1962 | Egler et al. . |
| 3,136,418 | 6/1964 | Stacy et al. . |
| 3,167,895 | 2/1965 | Egler et al. . |
| 3,280,971 | 10/1966 | Regan, Jr. . |
| 3,301,393 | 1/1967 | Regan, Jr. et al. ............... 206/63.3 |
| 3,338,401 | 8/1967 | Regan, Jr. . |
| 3,490,192 | 1/1970 | Regan, Jr. . |
| 3,495,703 | 2/1970 | Calabrese ........................ 206/63.3 |
| 3,545,608 | 12/1970 | Berger et al. . |
| 3,627,120 | 12/1971 | Bourdeau . |
| 3,731,793 | 5/1973 | Hagel ............................... 206/63.3 |
| 3,759,376 | 9/1973 | Lisowski . |
| 3,768,635 | 10/1973 | Eggert . |
| 3,876,068 | 4/1975 | Sonnino . |
| 3,939,969 | 2/1976 | Miller et al. . |
| 3,959,947 | 6/1976 | Sonnino . |
| 3,972,418 | 8/1976 | Schuler et al. . |
| 4,034,850 | 7/1977 | Mandel et al. . |
| 4,063,638 | 12/1977 | Marwood . |
| 4,084,692 | 4/1978 | Bilweis . |
| 4,116,333 | 9/1978 | Pavel . |
| 4,183,431 | 1/1980 | Schmidt et al. . |
| 4,249,656 | 2/1981 | Cerwin et al. . |
| 4,253,563 | 3/1981 | Komarnycky . |
| 4,369,880 | 1/1983 | Giggey et al. . |
| 4,406,363 | 9/1983 | Aday . |
| 4,412,613 | 11/1983 | Kubas . |
| 4,412,614 | 11/1983 | Ivanou et al. . |
| 4,418,821 | 12/1983 | Sandel . |
| 4,424,898 | 1/1984 | Thyen et al. . |
| 4,427,109 | 1/1984 | Roshdy . |
| 4,496,045 | 1/1985 | Ferguson et al. . |
| 4,573,575 | 3/1986 | Bergrath et al. . |
| 4,574,948 | 3/1986 | Huck et al. . |
| 4,699,271 | 10/1987 | Lincoln et al. . |
| 4,802,581 | 2/1989 | Takahashi . |
| 4,961,498 | 10/1990 | Kalinski et al. . |
| 4,967,902 | 11/1990 | Sobel et al. . |
| 5,048,678 | 9/1991 | Chambers . |
| 5,052,551 | 10/1991 | Cerwin et al. . |
| 5,056,658 | 10/1991 | Sobel et al. . |
| 5,078,730 | 1/1992 | Li et al. . |
| 5,086,914 | 2/1992 | Mish et al. . |
| 5,099,994 | 3/1992 | Kalinski et al. . |
| 5,101,968 | 4/1992 | Henderson et al. . |
| 5,123,528 | 6/1992 | Brown et al. . |
| 5,131,533 | 7/1992 | Alpern . |
| 5,154,283 | 10/1992 | Brown . |
| 5,192,483 | 3/1993 | Kilgrow et al. . |
| 5,228,565 | 7/1993 | Sinn ................................ 206/63.3 |

(List continued on next page.)

FOREIGN PATENT DOCUMENTS 2161130  1/1986  United Kingdom .

*Primary Examiner*—Jimmy G. Foster

[57] ABSTRACT

A suture package is provided having a body portion defining an inner cavity and a cover plate affixed to the body for retention of a coiled length of suture therebetween and having an exit area configured to prevent kinking of the coils of suture upon removal of the suture from the package. A loading unit for use with a surgical suturing apparatus is provided having a body portion defining an inner cavity, a cover plate affixed to the body portion for retention of a coiled length of suture therebetween and having an exit area configured to prevent kinking of the coils of the suture upon removal, and a mounting member positioned on the body portion and configured to releasably hold a surgical needle.

28 Claims, 5 Drawing Sheets

U.S. PATENT DOCUMENTS

| | | | |
|---|---|---|---|
| 5,249,671 | 10/1993 | Sinn | 206/63.3 |
| 5,271,495 | 12/1993 | Alpern | |
| 5,392,903 | 2/1995 | Sinn | 206/63.3 |
| 5,437,362 | 8/1995 | Sinn | 206/63.3 |
| 5,478,344 | 12/1995 | Stone et al. | 206/63.3 |
| 5,503,266 | 4/1996 | Kalbfeld et al. | 206/63.3 |

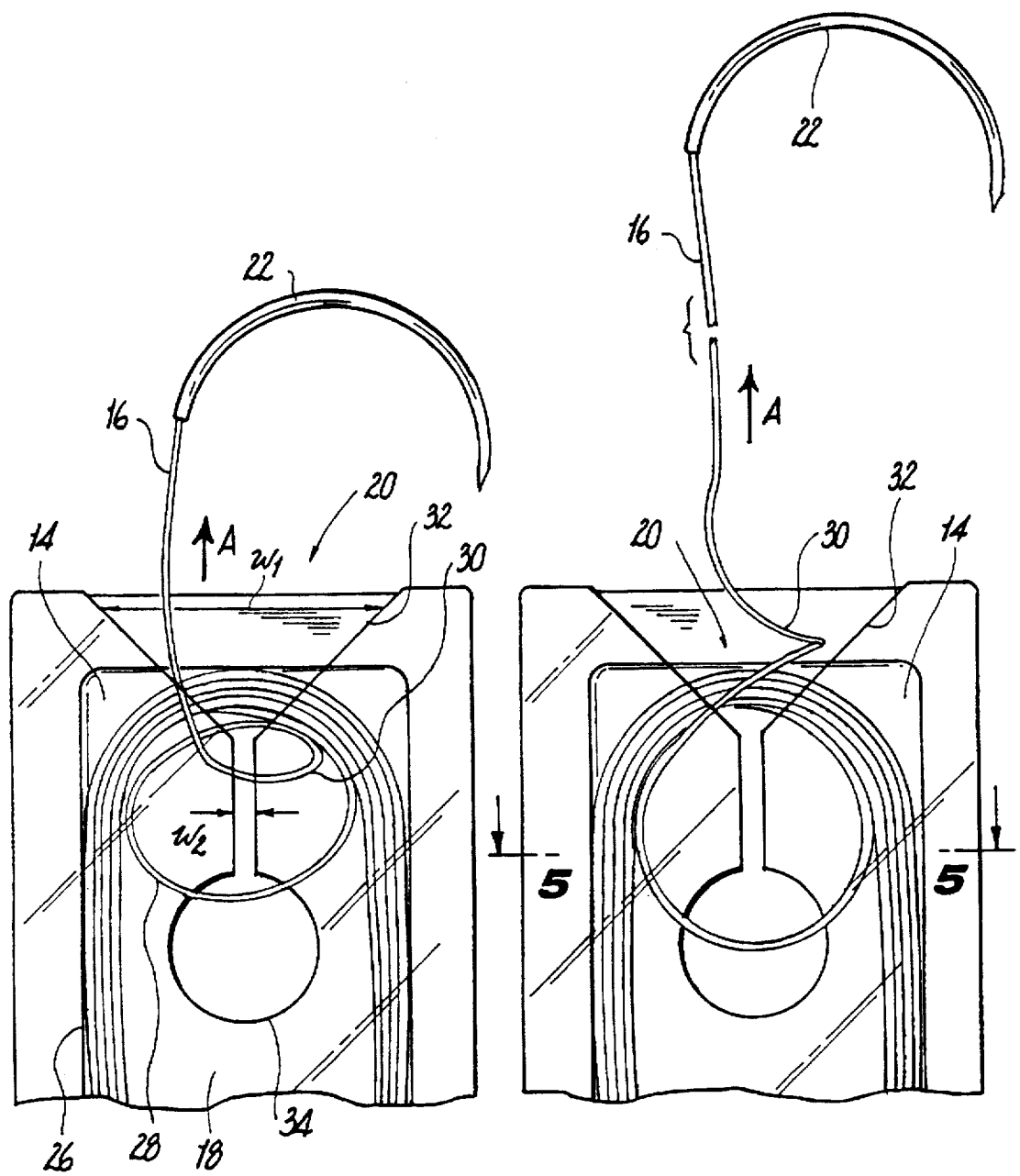
Fig. 3  Fig. 4
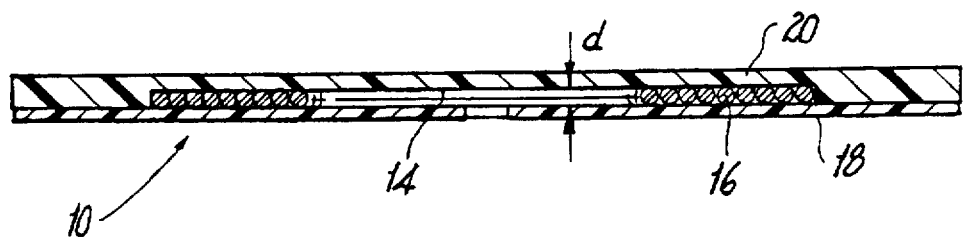
Fig. 5

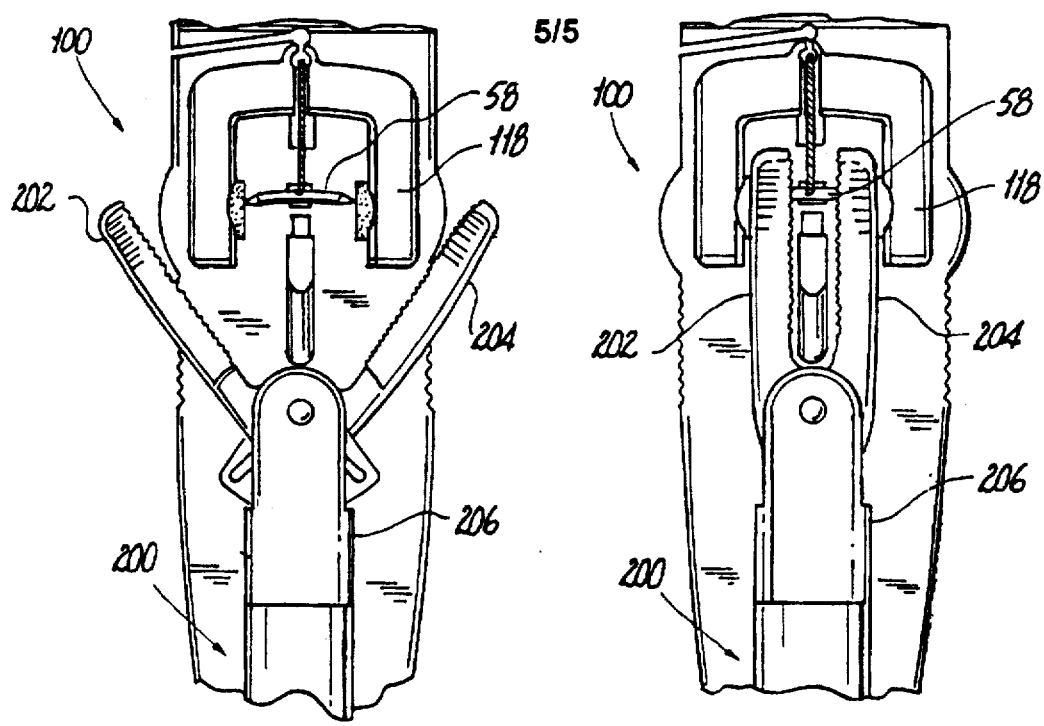
Fig. 12  Fig. 13
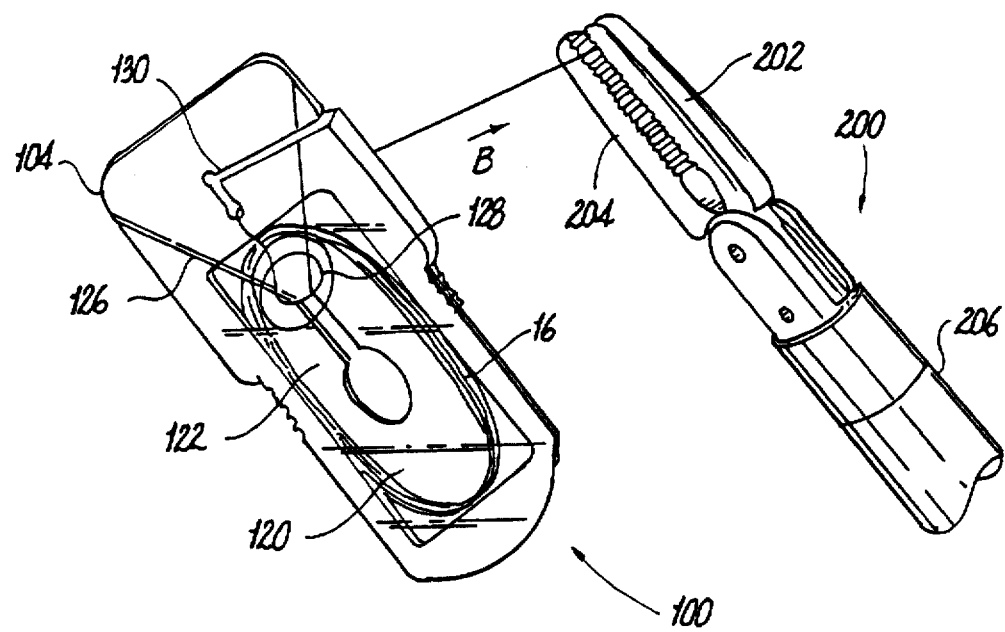
Fig. 14

SUTURE RETAINER

BACKGROUND

1. Technical Field

The technical field relates generally to surgical suture retainers and, more particularly, to an improved suture package for retaining sutures to improve handling characteristics thereof.

2. Description of Related Art

Various types and styles of suture retainers have been developed to hold surgical needles and associated length of suture for use during a surgical operation. Generally, a suture retainer should be constructed to adequately secure a needle and suture while providing easy withdrawal during use. It is also preferable to minimize permanent deformation of the suture by kinking or bending during storage and removal from the suture retainer.

Suture retainers typically include a folded pouch containing a single needle and suture combination. To access the needle and suture, the package is at least partially unfolded and the needle-suture is removed. The suture is typically wound in an oval or figure "8" pattern within the retainer. The needle can be secured in a slot or die cut formed in the pouch or, in the alternative, can piercingly engage a foam strip affixed to the pouch.

Another type of retainer is of molded construction, such as, for example, the retainer disclosed in U.S. Pat. No. 5,154,283 to Brown. The retainer described in the Brown patent includes a molded cover member having a spiraled passageway formed therein to accommodate a suture and a cover sheet adhered to the molded member to close the passageway.

Sometimes, surgical sutures are intended for use with a surgical apparatus. When this is the case, it is often necessary to manually remove the needle-suture combination by hand and insert them into the apparatus. A dispenser for holding surgical needles and anchors is disclosed in U.S. Pat. No. 4,821,878 to Jones. The Jones dispenser is configured to hold the needle and anchor in a position to be grasped by a manipulating tool.

A suture package, or loading unit, to facilitate the removal of a needle and a length of suture by a suture applying apparatus is described in commonly assigned U.S. patent application Ser. No. 08/293,234, filed Aug. 19, 1994, which is incorporated herein by reference. Another loading unit for supporting a needle is disclosed in commonly-assigned U.S. patent application Ser. No. 08/293,233, filed Aug. 19, 1994.

Many surgical procedures call for placing stitches through tissue, a procedure traditionally accomplished by hand. It is desirable to remotely join tissue together by passing a needle, having a length of suture material attached thereto, back and forth between jaws located on opposite sides of the tissues. One such device is the "ENDO STITCH" suturing device manufactured by United States Surgical Corporation, Norwalk, Conn. This tissue-stitching instrument includes a pair of jaws configured to alternately receive opposed ends of a needle. The needle with an attached length of suture is passed alternately back and forth between the jaws to remotely stitch tissue together. This surgical apparatus is suited for endoscopic or laparoscopic suturing because it is configured to be inserted through a port that typically averages between five and ten millimeters. During many endoscopic procedures, it is necessary to rapidly and accurately place successive needle-suture combinations using sutures of various lengths within the jaws of a surgical suturing apparatus for immediate and repeated use during the surgical procedure. Further, it is often necessary to grasp the needles at specific locations along the needle body to facilitate suturing such as, for example, at one end or the other. Thus, it is desirable to have a needle and suture supplying device which is capable of supplying a needle and positioning it within the jaws of a surgical suturing apparatus. It is also desirable to have a suture storage area to maintain a length of the suture therein for easy withdrawal from the storage member during surgical procedures. However, the suture material can close upon itself and kink or bend during withdrawal from the suture storage member. It is therefore desirable to provide a suture storage area configured to release the suture therefrom before such kinking occurs.

SUMMARY

In one embodiment, the disclosed surgical suture package stores a length of suture and a surgical needle. The suture package generally includes a body portion having a rigid construction and defining an inner cavity, a cover plate affixed to the body portion for retention of a coiled length of suture therebetween. The cover plate has an exit area configured to prevent kinking of the coils of the suture. The suture package further includes a needle park positioned on the body portion configured to releasably hold a surgical needle.

In another embodiment, a loading unit is disclosed for storing a length of suture and for positioning a surgical needle for mounting in the jaws of a surgical suturing instrument. The loading unit generally includes a body portion defining an inner cavity, a cover plate affixed to the body portion for retention of a coiled length of suture therebetween. The cover plate has an exit area configured to prevent kinking of the coils of the suture. The loading unit further includes a mounting member positioned on the body portion and configured to releasably hold a surgical needle.

Preferably, the exit area is a notched portion. A partial removal of the suture from the inner cavity progressively reduces the size of an innermost coiled portion of the suture. The notched portion of the exit area is configured to release the innermost coiled portion from the inner cavity prior to kinking of the suture. The inner cavity and the cover plate are configured to inhibit a first portion of the suture from overlapping a second portion of the suture when the suture is disposed within the inner cavity exclusive of the exit area. Preferably, the inner cavity has a depth measuring less than two diameters of the suture.

BRIEF DESCRIPTION OF THE DRAWINGS

Various embodiments are described herein with reference to the drawings, wherein:

FIG. 3 is a partial plan view of the suture package, illustrating removal of a coiled portion of the suture from the suture package;

FIG. 4 is a partial plan view of the suture package, illustrating a coiled portion of the suture subsequent to removal from the suture package;

FIG. 5 is a cross-sectional view of the suture package taken along line 5—5 of FIG. 4;

FIG. 12 is a top plan view of the embodiment of FIG. 8 indicating the placement of a suturing apparatus thereon;

FIG. 13 is a top plan view of the embodiment of FIG. 8 indicating the closure of jaw portions of the suturing apparatus about a surgical needle held in position by the suture package; and FIG. 14 is a perspective view illustrating the removal of the suture from the embodiment of FIG. 8 by the suturing apparatus.

DESCRIPTION OF PREFERRED EMBODIMENTS

Figure 1:
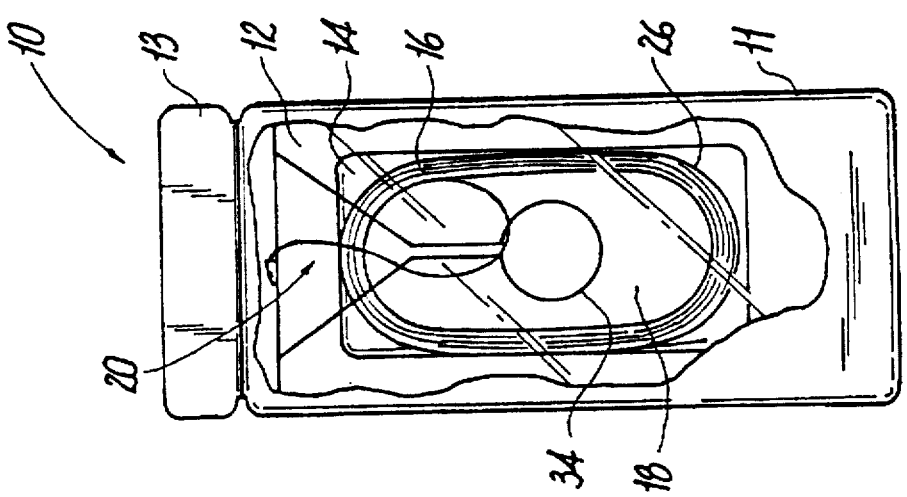
FIG. 1 is a back plan view of one embodiment of a suture package illustrating a cover plate and a coiled length of suture.

Referring to FIG. 1, there is shown a first, preferred embodiment of a suture package generally indicated by reference numeral 10. Package 10 is particularly configured to accommodate a length of suture for removal therefrom without undesirable deformation of the suture, and to retain a needle attached to the suture in a readily accessible position adjacent the suture package wherein the needle is grasped by hand or needle graspers as is known in the art. Package 10 is preferably disposed in sleeve 11 with flap 13 for sterilization and storage.

Package 10 includes body portion 12, preferably formed of a rigid plastic material, which defines an inner cavity 14 for storing a length of suture 16 therein. A cover plate 18 is glued to the body portion 12 or affixed by any known method to retain suture 16 within inner cavity 14. Cover plate 18 is configured to define an exit area 20 to facilitate removal of suture 16, as will be described in greater detail below.

A circular loading hole 34 is further provided in cover plate 18 to facilitate insertion of suture 16 within inner cavity 14. Suture 16 can be loaded into suture package 10 through loading hole 34 either manually or by a known mechanical feed. Preferably, suture package 10 is rotated relative to suture 16 during loading to create coiled configuration 26 of suture 16 within inner cavity 14.

Figure 2:
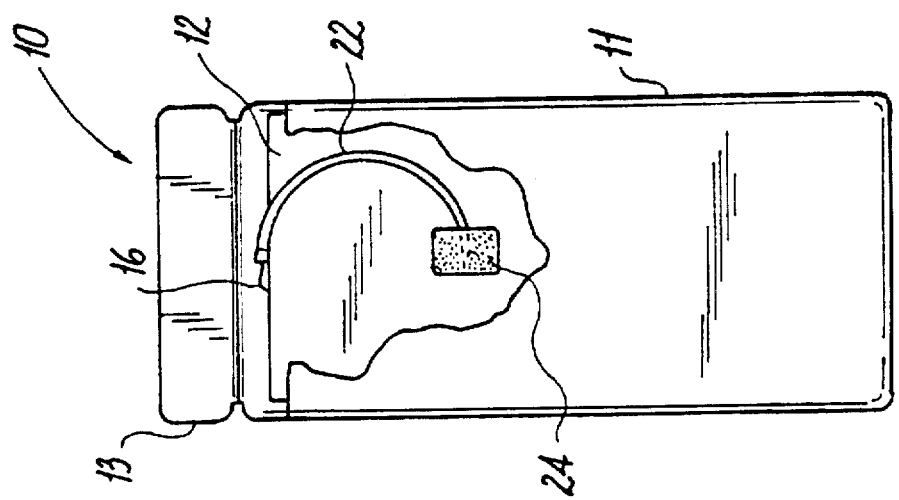
FIG. 2 is a front plan view of the embodiment of the suture package of FIG. 1 illustrating the needle and needle park.

As shown in FIG. 2, the preferred suture package 10 is provided with a needle 22 affixed to an end portion of suture 16. A needle park 24 can be provided on body portion 12 for holding needle 22 in place during storage.

Referring now to FIGS. 3 and 4, progressive removal of suture 16 from inner cavity 14 is illustrated. Suture 16 is stored in cavity 14 in a coiled configuration, as designated by numeral 26. Withdrawal of suture 16, as indicated by arrow "A", progressively reduces the size of an inner coil 28. Further reduction of the radius of suture coils below a predetermined limit can produce a deformation, or kinking to suture 16 as suture 16 overlaps itself.

Cover plate 18, which is preferably constructed of a moldable transparent plastic material, is configured to release innermost suture coil 30 from inner cavity 14 prior to deformation thereof. FIG. 4 illustrates innermost suture coil 30 subsequent to release from exit area 20 prior to kinking. Exit area 20 partially exposes a portion of suture 16. Exit area 20 is preferably a notched portion which overlies the suture coils 26 and is aligned radially therewith. The notched portion has a first width "$w_1$", and a second width "$w_2$". In the preferred embodiment, first width "$w_1$", is larger than second width "$w_2$". The edges 32 of the exit area 20 are depicted in FIG. 3 as linear and generally Y-shaped, although edges 32 can be curved or multi-lateral. It is also contemplated that "$w_1$" and "$w_2$" can be substantially equal to define a rectangular exit area. The dimensions of "$w_1$" and "$w_2$" are selected based upon the material characteristics of suture 16, such that coil 30 is uncovered from edge portion 32 prior to undesirable deformation.

Referring now to FIG. 5, inner cavity 14 is defined by a depression machined or molded within body portion 20, and cover sheet 18. Inner cavity 14 has a depth "d", which preferably measures less than two diameters of suture 16 loaded therein. The selected depth "d" assists in maintaining suture 16 in the coiled configuration by inhibiting overlapping of sections of suture 16 in inner cavity 14. Exit area 20, however, permits overlap of suture 16 during removal.

Figure 6:
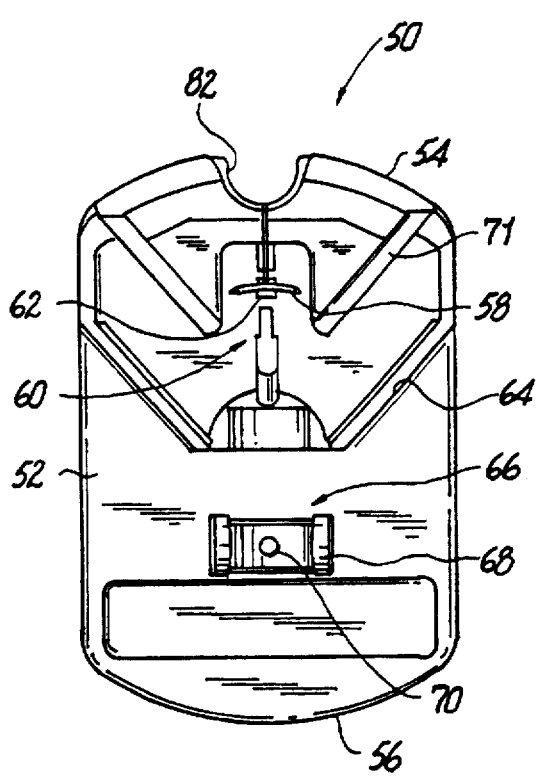
FIG. 6 is a top plan view of an alternate embodiment of the suture package.
Figure 7:
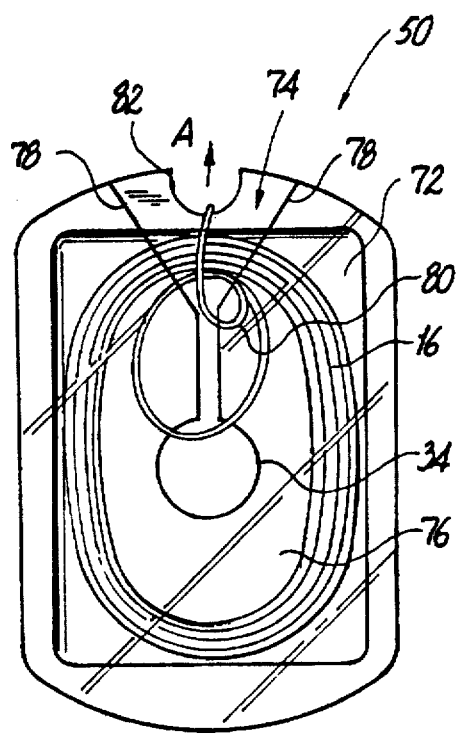
FIG. 7 is a bottom plan view of the embodiment of FIG. 6.
Figure 10:
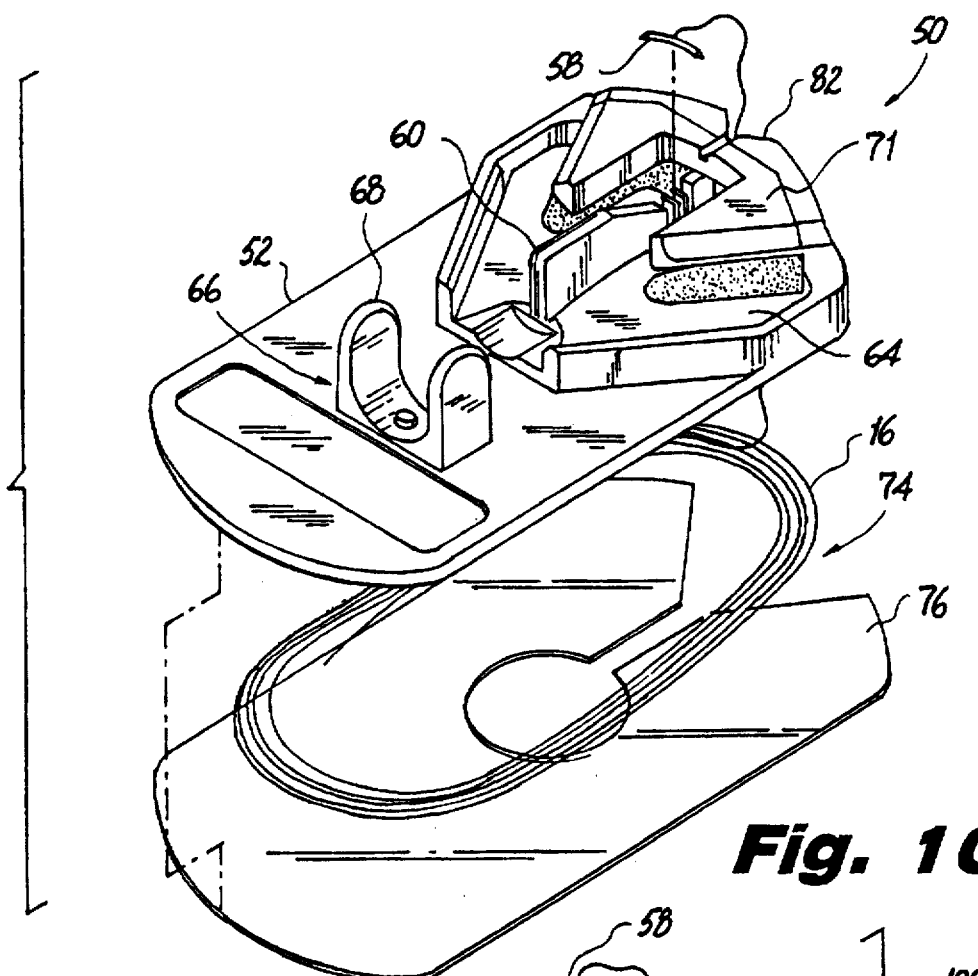
FIG. 10 is a perspective view with parts separated of the embodiment of FIG. 6.

FIGS. 6–7 and 10 illustrate an alternate embodiment of a suture retainer designated generally by numeral 50. The suture retainer or loading unit 50 generally includes a body portion 52. As used herein with reference to loading unit 50, the proximal portion 54 of loading unit 50 is located toward the holding hand of the user, and the distal portion 56 refers the opposite end.

Loading unit 50 is provided to support a needle 58 in a manner to facilitate gripping or loading needle into a surgical suturing instrument. Thus, loading unit 50 includes a needle support member 60 formed on body portion 52 to support or suspend needle 58 by a central portion thereof. Preferably, support member 60 includes a pair of flexible fingers 62 which hold a central portion of needle 58. Apparatus receiving structure can be provided to guide the jaws of a suturing apparatus adjacent support member 60. The apparatus receiving structure can include a pair of jaw support shelves 64 defining a pair of recesses adjacent support member 60 to align jaw members to grasp needle 58.

Additionally, the apparatus receiving structure can include various other alignment structure to guide or orient the jaws of a surgical suturing apparatus into position on loading unit 50 to grasp and remove needle 58. For example, an elongate member alignment structure 66 can be provided to guide a barrel housing or elongate portion of a suturing instrument into position on loading unit 50. Alignment structure 66 generally includes a pair of side tabs 68 which surround the suture apparatus elongate portion. Additionally, a support stud 70 can be provided to maintain the elongate portion in proper vertical alignment with a corresponding recess in the suture apparatus elongate portion. Support stud 70 can also cooperate with corresponding structure on the elongate member to properly index the jaws with the needle. Blocking members 71 prevent removal of the jaws of suturing instrument from the loading unit 50 until the jaws are firmly closed, grasping needle 58.

FIG. 7 illustrates the coiled length of suture 16 stored within an inner cavity 72 on the underside of body portion 52. As described hereinabove with respect to suture package 10, the removal of suture 16 in the direction of arrow "A" is facilitated by the configuration of exit area 74 of cover plate 76. Exit area 74 is preferably a notched portion which partially exposes suture 16. The notched portion includes edges 78 aligned to uncover and release an innermost coil 80 of suture 16 from cavity 72 prior to kinking of suture 16. Edge 78 can be linear, as illustrated in FIG. 7. Alternatively, edges 78 can be curved to define a circular exit area 74, or multi-lateral to define a rectangular exit area 74. A guide notch 82 is formed at a proximal portion of loading unit 50 in order to convey suture 16 from inner cavity 72 to the needle support member 60. Loading hole 34 in cover plate 76 facilitates loading of suture 16 into cavity 72 as described above.

FIG. 10 further illustrates the relative placement of suture 16 between body portion 52 of loading unit 50 and cover plate 76. As described above, a portion of suture 16 is positioned in cavity 72 and conveyed over guide notch 82 to support member 60, in which an end portion of suture 16 is affixed to needle 58 held by support member 60.

Figure 8:
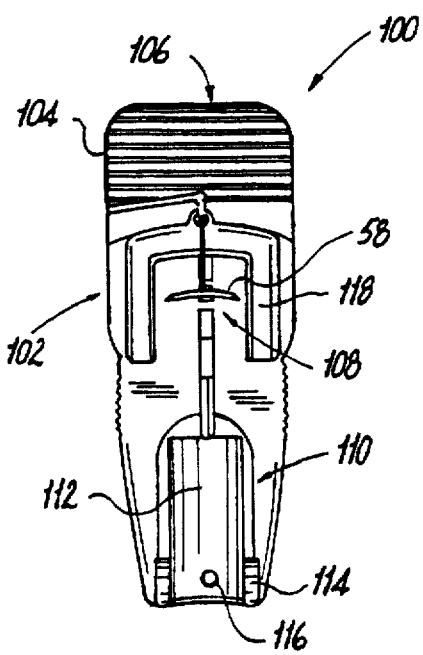
FIG. 8 is a top plan view of another alternate embodiment of the suture package viewed from above.
Figure 9:
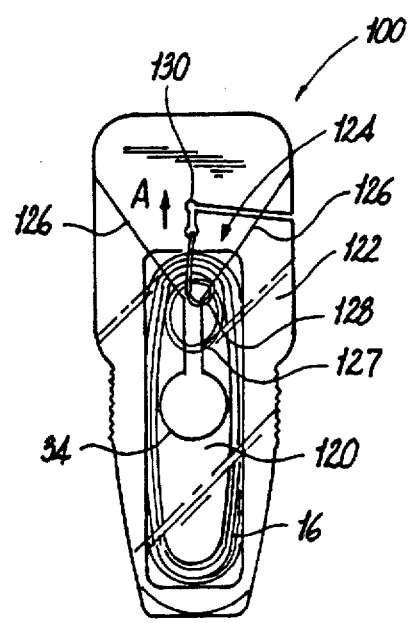
FIG. 9 is a bottom plan view of the embodiment of FIG. 8.
Figure 11:
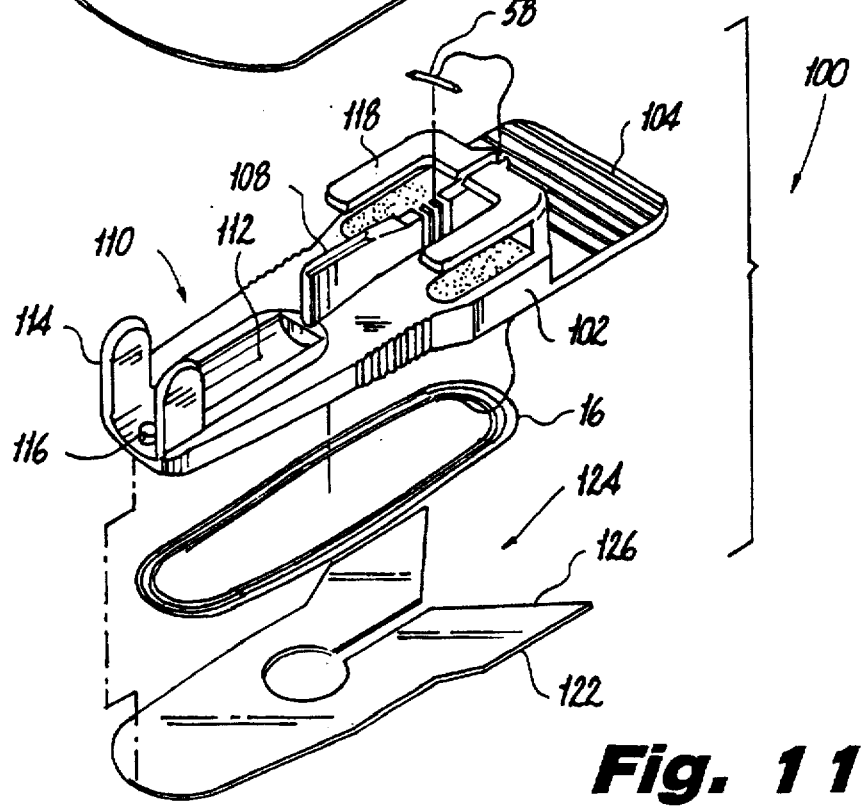
FIG. 11 is a perspective view with parts separated of the embodiment of FIG. 8.

Turning now to FIGS. 8–9 and 11, there is illustrated yet another embodiment of the suture retainer or loading unit in accordance with the present apparatus, designated generally at 100. The loading unit 100 includes a body portion 102 having a handle or finger tab 104 extending from proximal portion 106 thereof. Preferably, finger tab 104 includes a plurality of ridges, or be otherwise textured, to enhance the gripping ability of the user.

Loading unit 100 is provided with support member 108 for releasably supporting needle 58. Apparatus receiving structure can be provided to guide the jaws of suturing apparatus adjacent support member 108. Such apparatus receiving structure can include alignment structure 110 to guide a barrel housing or elongate portion of a suturing instrument into position in loading unit 100. Alignment structure 110 generally includes a recess or cup 112 and a pair of side tabs 114 which surround the suture apparatus elongate portion. The alignment structure preferably includes a support stud 116 to cooperate with a corresponding recess in the elongate portion to achieve proper alignment therewith. Blocking members 118 are provided to prevent removal of the jaws of the suturing instrument from loading unit 100 until the jaws are closed, firmly grasping needle 58.

FIG. 9 illustrates the coiled length of suture 16 stored within inner cavity 120 and enclosed by cover plate 122. The removal of suture 16 in the direction of arrow "A" is facilitated by the configuration of exit area 124 of cover plate 122. Exit area 124 is preferably a notched portion which partially exposes suture 16. The notched portion includes edges 126 which can have a linear configuration, as illustrated in FIG. 9. Edges 126 can alternatively be curved or multi-lateral. Exit area 124 of cover plate 122 is configured to release suture 16 from cavity 120 prior to kinking of the suture 16. Withdrawal of suture 16 progressively reduces the size of suture coils 127 as described above with respect to retainer 10. Edges 126 are aligned with suture 16 to uncover an innermost suture coil 128 from cavity 120 before further reduction of coil 128 causes kinking thereof. A guide notch 130 is formed at a proximal portion of loading unit 100 to convey suture 16 from inner cavity 120 to the needle support member 108.

FIG. 11 further illustrates the relative placement of suture 16 between body portion 102 of loading unit 100 and cover plate 122. A portion of suture 16 is positioned in cavity 120 (FIG. 9) and conveyed over guide notch 130 to support member 108, in which an end portion of suture 16 is affixed to needle 58 held by support member 108.

FIGS. 12–14 illustrate a method for grasping surgical needle 58 from loading unit 100 and subsequent removal of coils of suture 16 therefrom without kinking or bending. The procedure described hereinbelow is substantially identical when performed in conjunction with loading unit 50 described above. Surgical suturing apparatus, designated generally at 200, includes a pair of jaws 202 and 204 mounted on an elongate body portion 206. Suturing apparatus 200 is brought into approximation with loading unit 100 as illustrated in FIG. 12. Alignment structure 110 guides elongate portion 206 into alignment with loading unit 100, while jaws 202 and 204 are maintained in an open position. Subsequently, jaws 202 and 204 are approximated into closed position of FIG. 13, thereby firmly grasping needle 58 by means of needle grasping structure provided thereon. Suturing apparatus is subsequently removed from loading unit 100, provided jaws 202 and 204 are sufficiently closed to clear blocking members 118.

FIG. 14 illustrates further displacement of suturing apparatus 200 from loading unit 100 in the direction of arrow "B". As progressive withdrawal of suture 16 from inner cavity 120 reduces the size of innermost coil 128, the alignment of edges 126 release coil 128 from cavity 120 by uncovering coil 128 prior to kinking of suture 16.

It will be understood that various modifications can be made to the embodiments disclosed herein. For example, the exit area can incorporate various curvilinear or angular configurations and various ratios of widths $w_1/w_2$ (i.e. 1/1 to form rectangular exit area) to release the suture material without deforming it. Therefore, the above description should not be construed as limiting but merely as exemplifications of preferred embodiments. Those skilled in the art will envision other modifications within the scope and spirit of the claims appended hereto.

What is claimed is:

1. A loading unit for use with a surgical suturing apparatus comprising:
   a) a surgical needle secured to a length of coiled suture having; an innermost coiled portion;
   b) a body portion defining an inner cavity;
   c) a cover plate affixed to the body portion for removable retention of the coiled length of suture therebetween, the cover plate having an exit area configured to prevent kinking of the coils of the suture upon removal, the exit area including an open generally Y-shaped notched portion configured to release the innermost coiled portion of the suture from the inner cavity prior to kinking of the suture; and
   d) a mounting member positioned on the body portion and configured to releasably hold the surgical needle.

2. The loading unit of claim 1, wherein the innermost coiled portion of the suture is progressively reduced in size in response to at least partial removal of the suture.

3. The loading unit of claim 1, wherein the notched portion is radially aligned with the coiled portion of the suture.

4. The loading unit of claim 3, wherein the notched portion overlies at least a portion of the coiled portion of the suture.

5. The loading unit of claim 1, wherein the notched portion has a first width and a second width.

6. The loading unit of claim 5, wherein the first width of the notch portion is greater than the second width.

7. The loading unit of claim 6, wherein the first width is disposed further from the center of the coiled length of suture than the second width.

8. The loading unit of claim 1, wherein the inner cavity has a depth measuring less than two diameters of the suture.

9. The loading unit of claim 1, wherein the inner cavity and the cover plate are configured to inhibit a first portion of the suture from overlapping with a second portion of the suture when the suture is disposed within the inner cavity exclusive of the exit area.

10. The loading unit of claim 1, wherein the cover plate comprises a moldable transparent plastic material.

11. The loading unit of claim 1, wherein the cover plate has a loading hole communicating with the inner cavity.

12. A loading unit for use with a surgical suturing apparatus comprising:
   a) a surgical needle secured to a length of coiled suture;
   b) a body portion defining an inner cavity;
   c) a cover plate affixed to the body portion for retention of the length of suture therebetween, the cover plate exposing a portion of the inner cavity to facilitate removal of the suture from the cavity;
   d) a mounting member positioned on the body portion and configured to releasably hold the surgical needle; and
   e) apparatus receiving structure formed in the body portion wherein the apparatus receiving structure is configured to receive at least a distal end portion of the surgical suturing apparatus in operative alignment with the mounting member to facilitate mounting of the surgical needle in the surgical suturing apparatus.

13. The loading unit of claim 12, wherein at least a portion of the length of suture is disposed in the inner cavity in a coiled configuration.

14. The loading unit of claim 13, wherein the inner cavity and the cover plate are configured to inhibit the overlapping of a first portion of suture with a second portion of suture when the suture is disposed within the inner cavity exclusive of the exit area.

15. The loading unit of claim 14, wherein partial removal of the suture from the cavity progressively reduces the size of an innermost coiled portion and the cover plate is configured to expose the innermost coiled portion prior to kinking of the suture.

16. The loading unit of claim 12, wherein the cover plate comprises a moldable transparent plastic material.

17. The loading unit of claim 12, wherein the cover plate has a loading hole communicating with the inner cavity formed therein.

18. A suture package comprising:
   a) a length of suture;
   b) a body portion defining an inner cavity; and
   c) a cover plate affixed to the body portion for retention of the length of suture therebetween, the cover plate having an exit area which includes an open generally Y-shaped notched portion configured to prevent kinking of the suture upon removal from the exit area of the suture package.

19. The suture package of claim 18, wherein the length of suture is removably disposed within the package in a coil configuration having an innermost portion progressively reduced in size in response to at least partial removal of the suture from the inner cavity.

20. The suture package of claim 19, wherein the notched portion is configured to release the innermost coiled portion from the inner cavity prior to kinking of the suture.

21. The suture package of claim 18, wherein the notched portion has a first width and a second width.

22. The suture package of claim 21, wherein the first width of the notched portion is greater than the second width.

23. The suture package of claim 22, wherein the first width is disposed furthest from the center of the coiled length of suture than the second width.

24. The suture package of claim 18, wherein the inner cavity has a depth measuring less than two diameters of the suture.

25. The suture package of claim 18, wherein the inner cavity and the cover plate are configured to inhibit a first portion of the suture from overlapping with a second portion of the suture when the suture is disposed within the inner cavity exclusive of the exit area.

26. The suture package of claim 18, further comprising a needle park positioned on the body portion.

27. The suture package of claim 18, wherein the cover plate comprises a moldable transparent plastic material.

28. The suture package of claim 18, wherein the cover plate has a loading hole communicating with the inner cavity formed therein.

* * * * *